United States Patent [19]

Buckley

[11] Patent Number: 4,710,201

[45] Date of Patent: Dec. 1, 1987

[54] MODIFIED SUCCINIMIDES (IX)

[75] Inventor: Thomas F. Buckley, Hercules, Calif.

[73] Assignee: Chevron Research Company, San Francisco, Calif.

[21] Appl. No.: 28,351

[22] Filed: Mar. 20, 1987

Related U.S. Application Data

[60] Division of Ser. No. 904,086, Sep. 4, 1986, which is a continuation-in-part of Ser. No. 820,457, Jan. 17, 1986, abandoned.

[51] Int. Cl.$^4$ .......................... C10L 1/18; C10L 1/22
[52] U.S. Cl. ........................................... 44/63; 44/73; 44/57
[58] Field of Search .............................. 44/63, 73, 57

[56] References Cited

U.S. PATENT DOCUMENTS

| | | | |
|---|---|---|---|
| 2,802,022 | 8/1957 | Groszos et al. | 260/471 |
| 2,844,449 | 7/1958 | Dille et al. | 44/70 |
| 2,991,162 | 7/1961 | Malec | 44/58 |
| 3,216,936 | 11/1965 | Le Suer | 252/32.7 |
| 3,367,943 | 2/1968 | Miller et al. | 260/326.3 |
| 3,373,111 | 3/1968 | Le Suer et al. | 252/51.5 |
| 3,652,240 | 3/1972 | Dorn et al. | 44/66 |
| 4,191,537 | 3/1980 | Lewis | 44/71 |
| 4,322,305 | 3/1982 | Lewis | 252/51.5 A |
| 4,460,381 | 7/1984 | Karol et al. | 44/63 |
| 4,482,464 | 11/1984 | Karol et al. | 252/51.5 A |
| 4,490,154 | 12/1984 | Sung et al. | 44/70 |
| 4,501,597 | 2/1985 | Karol et al. | 44/63 |
| 4,581,038 | 4/1986 | Hoke | 44/63 |
| 4,581,040 | 4/1986 | Sung et al. | 44/63 |
| 4,585,566 | 4/1986 | Wollenberg | 252/51.5 A |
| 4,608,185 | 8/1986 | Buckley | 252/51.5 A |
| 4,612,132 | 9/1986 | Wollenberg et al. | 252/51.5 A |
| 4,614,522 | 9/1986 | Buckley | 44/63 |
| 4,645,515 | 2/1987 | Wollenberg | 44/63 |
| 4,647,390 | 3/1987 | Buckley et al. | 252/51.5 A |
| 4,648,886 | 3/1987 | Buckley et al. | 44/63 |

FOREIGN PATENT DOCUMENTS 689705 4/1953 United Kingdom .

*Primary Examiner*—Jacqueline V. Howard
*Attorney, Agent, or Firm*—S. R. LaPaglia; R. C. Gaffney; G. F. Swiss

[57] ABSTRACT

Disclosed are additives which are useful as dispersants in marine crankcase oils, hydraulic oils, and lubricating oils. In particular, disclosed are polyamino alkenyl or alkyl succinimides modified by reaction with a compound of the formula:

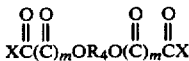

wherein $R_4$ is selected from the group consisting of a divalent hydrocarbyl group of from 2 to 30 carbon atoms with the proviso that the hydrocarbyl carbon atom bound to one

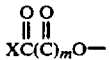

group is not also bound to the other

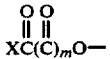

group and $-R_5(-OR_5)_p$ wherein $R_5$ is alkylene of from 2 to 5 carbon atoms and p is an integer of from 1 to 100; X is selected from the group consisting of bromo, chloro and $-OR_6$ wherein $R_6$ is selected from the group consisting of alkyl of from 1 to 6 carbon atoms, phenyl and phenyl substituted with 1 to 2 substituents selected from the group consisting of chloro, bromo, nitro, alkyl of from 1 to 6 carbon atoms and trifluoromethyl; and m is independently an integer of from 0 to 1.

39 Claims, No Drawings

MODIFIED SUCCINIMIDES (IX)

CROSS-REFERENCE TO RELATED APPLICATIONS

This is a division of application Ser. No. 904,086, filed Sept. 4, 1986, which in turn is a continuation-in-part of U.S. Ser No. 820,457, filed Jan. 17, 1986, now abandoned.

BACKGROUND OF THE INVENTION

1. Field of the Invention

This invention relates to additives which are useful as dispersants and/or detergents in lubricating oils and fuels. In particular, this invention is directed toward polyamino alkenyl or alkyl succinimides which have been modified by contacting said polyamino alkenyl or alkyl succinimide at a temperature sufficient to cause reaction with a compound of the formula:

wherein Rhd$_4$ is selected from the group consisting of a divalent hydrocarbyl group of from 2 to 30 carbon atoms with the proviso that the hydrocarbyl carbon atom bound to one

group is not also bound to the other

group and $-R_5(-OR_5)_p$ wherein $R_5$ is alkylene of from 2 to 5 carbon atoms and p is an integer of from 1 to 100; X is selected from the group consisting of bromo, chloro and $-OR_6$ wherein $R_6$ is selected from the group consisting of alkyl of from 1 to 6 carbon atoms, phenyl and phenyl substituted with 1 to 2 substituents selected from the group consisting of chloro, bromo, nitro, alkyl of from 1 to 6 carbon atoms and trifluoromethyl; and m is independently an integer of from 0 to 1.

The modified polyamino alkenyl or alkyl succinimides of this invention have been found to possess dispersancy and/or detergency properties when employed in a lubricating oil. These modified succinimides are also useful as detergents and/or dispersants in fuels.

2. Prior Art

Alkenyl or alkyl succinimides have been previously modified with alkylene oxides to produce poly(oxyalkylene)hydroxy derivatives thereof. These alkylene oxide-treated succinimides are taught as additives for lubricating oils (see U.S. Pat. Nos. 3,373,111 and 3,367,943). U.S. Pat. No. 2,991,162 discloses carburetor detergent additives for gasoline obtained by reacting an N-alkyl propylene diamine with ethylene carbonate to produce a two-component detergent additive consisting of a carbamate and a urea compound. U.S. Pat. No. 3,652,240 discloses carburetor detergent additives for hydrocarbonaceous fuel which are carbamates formed by the reaction of an amino-amide with ethylene carbonate. Karol et al., U.S. Pat. Nos. 4,501,597 and 4,460,381, disclose that the reaction product of oxalic acid with a mono- or bis-succinimide is useful as a fuel stabilizer and as a carburetor detergent. U.S. Pat. No. 4,482,464 discloses succinimides which have been modified by treatment with a hydroxyalkylene carboxylic acid selected from glycolic acid, lactic acid, 2-hydroxymethyl propionic acid and 2,2'-bis-hydroxy-methylpropionic acid. These modified succinimides of U.S. Pat. No. 4,482,464 are disclosed as lubricating oil additives. U.S. Pat. No. 4,490,154 discloses fuels containing an alkenylsuccinyl polyglycolcarbonate ester as a deposit control additive. U.S. Pat. No. 3,216,936 discloses a product prepared from an aliphatic amine, a polymer-substituted succinic acid and an aliphatic monocarboxylic acid. U.S. Pat. No. 4,191,537, among others, discloses hydrocarbyl-capped poly(oxyalkylene) polyamino carbamates useful as dispersants and detergents or fuels and lubricating oils.

SUMMARY OF THE INVENTION

It has now been found that polyamino alkenyl or alkyl succinimides may be modified by contacting at a temperature sufficient to cause reaction a polyamino alkenyl or alkyl succinimide having at least one primary or secondary amino group with a compound of Formula V:

wherein $R_4$ is selected from the group consisting of a divalent hydrocarbyl group of from 2 to 30 carbon atoms with the proviso that the hydrocarbyl carbon atom bound to one

group is not also bound to the other

group and $-R_5(-OR_5)_p$ wherein $R_5$ is alkylene of from 2 to 5 carbon atoms and p is an integer of from 1 to 100; X is selected from the group consisting of bromo, chloro and $-OR_6$ wherein $R_6$ is selected from the group consisting of alkyl of from 1 to 6 carbon atoms, phenyl and phenyl substituted with 1 to 2 substituents selected from the group consisting of chloro, bromo, nitro, alkyl of from 1 to 6 carbon atoms, and trifluoromethyl; m is independently an integer of from 0 to 1 and wherein the molar charge of the compound of Formula V to the basic nitrogen of the polyamino alkenyl or alkyl succinimide is from about 0.1:1 to about 0.5:1. These modified polyamino alkenyl or alkyl succinimides are dispersants and/or detergents for use in fuels or lubricating oils. Accordingly, the present invention also relates to a lubricating oil composition comprising a major amount of an oil of lubricating viscosity and an amount of a modified polyamino alkenyl or alkyl succinimide sufficient to provide dispersancy and/or detergency.

Another composition aspect of this invention is a fuel composition comprising a major portion of a hydrocarbon boiling in a gasoline or diesel range and an amount of a modified polyamino alkenyl or alkyl succinimide sufficient to provide dispersancy and/or detergency.

In one embodiment, $R_4$ is a divalent hydrocarbyl group of from 2 to 30 carbon atoms with the proviso that the hydrocarbyl carbon atom bound to one

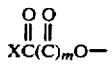

group is not also bound to the other

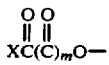

group. Preferred hydrocarbyl $R_4$ groups are alkylene groups of 2 to 30 carbon atoms. Such alkylene groups can be straight-chain alkylene groups of 2 to 30 carbon atoms or branched-chain alkylene groups of 3 to 30 atoms.

When $R_4$ is $-R_5(-OR_5)_p$, preferred embodiments include $C_2$-$C_4$ alkylene groups (i.e., $R_5$ is a $C_2$-$C_4$ alkylene group). Preferably, p is an integer of from 1 to 50; more preferably, p is an integer from 2 to 30 and most preferably, p is an integer from [b 2 to 20.

In general, the alkenyl or alkyl group of the succinimide is from 10 to 300 carbon atoms. While the modified succinimides of this invention possess good detergency properties even for alkenyl or alkyl groups of less than 20 carbon atoms, dispersancy is enhanced when the alkenyl or alkyl group is at least 20 carbon atoms. Accordingly, in a preferred embodiment, the alkenyl or alkyl group of the succinimide is at least 20 carbon atoms (i.e., the alkenyl or alkyl group is from 20 to 300 carbon atoms).

Preferably, $R_6$ is selected from the group consisting of phenyl or phenyl substituted with 1 to 2 substituents selected from chloro, bromo and alkyl of from 1 to 6 carbon atoms.

Hydrocarbyl, as used in describing the $R_4$ group, denotes a divalent organic radical composed of carbon and hydrogen which may be aliphatic, aromatic or combinations thereof. Suitable hydrocarbyls are alkylene such as ethylene ($-CH_2CH_2-$), 1,3-propylene ($-CH_2CH_2CH_2-$), 1,2-propylene $$(-CH_2CH-) \atop | \atop CH_3$$

etc; alkenylene such as propenyl, isobutenyl, etc. Preferably, the hydrocarbyl group will be relatively free of aliphatic unsaturation, i.e, ethylene and acetylenic, particularly acetylenic unsaturation.

As noted below, the

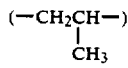

reagent is derived from from $HOR_4OH$. A carbon atom having 2 hydroxyyl groups is a hemiketal which readily loses water to from ketones (or aldehydes). Therefore, for the purpose of this invention, $R_4$ cannot have both hydroxy groups attached to the same carbon atom. Accordingly, in the

reagent, $R_4$ is a divalent hydrocarbyl group of from 2 to 30 carbon atoms with the proviso that the hydrocarbyl carbon atom bound to one

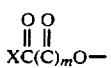

group is not also bound to the other

Straight-chain alkylene groups of from 2 to 30 carbon atoms refer to straight-chain alkylene groups such as 1,2-ethylene; 1,3-propylene; 1,5-pentalylene; 1,20-eiconsylene; 1,30-tricontylene; etc. Branched-chain alkylene groups of from 3 to 30 carbon atoms refer to branched-chain alkylene groups such as 1,2-propylene; 1,2-butylene; 1,2-(2-methyl)pentylene; 1,2-(2-ethyl) hexylene; 1,10-eiconsylene; etc.

DETAILED DESCRIPTION OF THE INVENTION

The modified polyamino alkenyl or alkyl succinimides of this invention are prepared from a polyamino alkenyl or alkyl succinimide. In turn, these materials are prepared by reacting an alkenyl or alkyl succinic anhydride with a polyamine as shown below:

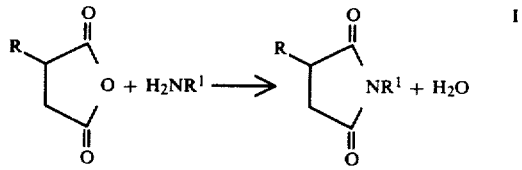

wherein R is an alkenyl or alkyl group of from 10 to 300 carbon atoms; and $R^1$ is the remainder of the polyamino moiety.

These alkenyl or alkyl succinimides that can be used herein are disclosed in numerous references and are well known in the art. Certain fundamental types of succinimides and related materials encompassed by the term of art "succinimide" are taught in U.S. Pat. Nos. 2,992,708; 3,018,291; 3,024,237; 3,100,673; 3,219,666; 3,172,892; and 3,272,746, the disclosures of which are hereby incorporated by reference. The term "succinimide" is understood in the art to include many of the amide, imide and amidine species which are also formed by this reaction. The predominant product however is succinimide and this term has been generally accepted as meaning the product of a reaction of an alkenyl substituted succinic acid or anhydride with a polyamine as shown in the reaction above. As used herein, included within this term are the alkenyl or alkyl mono-, bis-succinimides and other higher analogs.

A(1) Succinic Anhydride

The preparation of the alkenyl-substituted succinic anhydride by reaction with a polyolefin and maleic anhydride has been described, e.g., U.S. Pat. Nos.

3,018,250 and 3,024,195. Such methods include the thermal reaction of the polyolefin with maleic anhydride and the reaction of a halogenated polyolefin, such as a chlorinated polyolefin, with maleic anhydride. Reduction of the alkenyl-substituted succinic anhydride yields the corresponding alkyl derivative. Alternatively, the alkenyl substituted succinic anhydride may be prepared as described in U.S. Pat. Nos. 4,388,471 and 4,450,281 which are totally incorporated herein by reference.

Polyolefin polymers for reaction with the maleic anhydride are polymers comprising a major amount of $C_2$ to $C_5$ mono-olefin, e.g., ethylene, propylene, butylene, isobutylene and pentene. The polymers can be homopolymers such as polyisobutylene as well as copolymers of 2 or more such olefins such as copolymers of: ethylene and propylene, butylene, and isobutylene, etc. Other copolymers include those in which a minor amount of the copolymer monomers, e.g., 1 to 20 mole percent is a $C_4$ to $C_8$ nonconjugated diolefin, e.g., a copolymer of isobutylene and butadiene or a copolymer of ethylene, propylene and 1,4-hexadiene, etc.

The polyolefin polymer, represented in Formula 1 as R, usually contains from about 10 to 300 carbon atoms, although preferably 20 to 300 carbon atoms. Other preferred embodiments include 12 to 100 carbon atoms and more preferably 20 to 100 carbon atoms.

A particularly preferred class of olefin polymers comprises the polybutenes, which are prepared by polymerization of one or more of 1-butene, 2-butene and isobutene. Especially desirable are polybutenes containing a substantial proportion of units derived from isobutene. The polybutene may contain minor amounts of butadiene which may or may not be incorporated in the polymer. Most often the isobutene units constitute 80%, preferably at least 90%, of the units in the polymer. These polybutenes are readily available commercial materials well known to those skilled in the art. Disclosures thereof will be found, for example, in U.S. Pat. Nos. 3,215,707; 3,231,587; 3,515,669; and 3,579,450, as well as U.S. Pat. No. 3,912,764. The above are incorporated by reference for their disclosures of suitable polybutenes.

In addition to the reaction of a polyolefin with maleic anhydride, many other alkylating hydrocarbons may likewise be used with maleic anhydride to produce alkenyl succinic anhydride. Other suitable alkylating hydrocarbons include cyclic, linear, branched and internal or alpha olefins with molecular weights in the range 100–4,500 or more with molecular weights in the range of 200–2,000 being more preferred. For example, alpha olefins obtained from the thermal cracking of paraffin wax. Generally, these olefins range from 5–20 carbon atoms in length. Another source of alpha olefins is the ethylene growth process which gives even number carbon olefins. Another source of olefins is by the dimerization of alpha olefins over an appropriate catalyst such as the well known Ziegler catalyst. Internal olefins are easily obtained by the isomerization of alpha olefins over a suitable catalyst such as silica.

A(2) Polyamine

The polyamine employed to prepare the polyamino alkenyl or alkyl succinimides is preferably a polyamine having from 2 to about 12 amine nitrogen atoms and from 2 to about 40 carbon atoms. The polyamine is reacted with an alkenyl or alkyl succinic anhydride to produce the polyamino alkenyl or alkyl succinimide, employed in this invention. The polyamine is so selected so as to provide at least one basic amine per succinimide. The polyamine preferably has a carbon-to-nitrogen ratio of from about 1:1 to about 10:1.

Since the reaction of the polyamino alkenyl or alkyl succinimide with

is believed to efficiently go through a primary or secondary amine, at least one of the basic amine nitrogens of the polyamino moiety of the polyamino alkenyl or alkyl succinimide must be either a primary or secondary amine.

The polyamino portion of the polyamino alkenyl or alkyl succinimide may be substituted with substituents selected from (A) hydrogen, (B) hydrocarbyl groups of from 1 to about 10 carbon atoms, (C) acyl groups of from 2 to about 10 carbon atoms, and (D) monoketo, monohydroxy, mononitro, monocyano, lower alkyl and lower alkoxy derivatives of (B) and (C). "Lower", as used in terms like lower alkyl or lower alkoxy, means a group containing from 1 to about 6 carbon atoms.

Hydrocarbyl, as used in describing the polyamine components of this invention, denotes an organic radical composed of carbon and hydrogen which may be aliphatic, alicyclic, aromatic or combinations thereof, e.g., aralkyl. Preferably, the hydrocarbyl group will be relatively free of aliphatic unsaturation, i.e., ethylenic and acetylenic, particularly acetylenic unsaturation. The substituted polyamines of the present invention are generally, but not necessarily, N-substituted polyamines. Exemplary hydrocarbyl groups and substituted hydrocarbyl groups include alkyls such as methyl, ethyl, propyl, butyl, isobutyl, pentyl, hexyl, octyl, etc., alkenyls such as propenyl, isobutenyl, hexenyl, octenyl, etc., ketoalkyls, such as 2-ketopropyl, 6-ketooctyl, etc., alkoxy and lower alkenoxy alkyls, such as ethoxyethyl, ethoxypropyl, propoxyethyl, propoxypropyl, 2-(2-ethoxyethoxy)ethyl, 2-[2-(2-ethoxyethoxy)ethoxy]ethyl, 3,6,9,12-tetraoxatetradecyl, 2-(2-ethoxyethoxy)hexyl, etc. The acyl groups of the aforementioned (C) substituents are such as propionyl, acetyl, etc. The more preferred substituents are hydrogen, $C_1$–$C_6$ alkyls, and $C_1$–$C_6$ hydroxyalkyl.

In a substituted polyamine the substituents are found at any atom capable of receiving them. The substituted atoms, e.g., substituted nitrogen atoms, are generally geometrically inequivalent, and consequently the substituted amines finding use in the present invention can be mixtures of mono- and polysubstituted polyamines with substituent groups situated at equivalent and/or inequivalent atoms.

The more preferred polyamine finding use within the scope of the present invention is a polyalkylene polyamine, including alkylene diamine, and including substituted polyamines, e.g., alkyl substituted polyalkylene polyamine. Preferably, the alkylene group contains from 2 to 6 carbon atoms, there being preferably from 2 to 3 carbon atoms between the nitrogen atoms. Such groups are exemplified by ethylene, 1,2-propylene, 2,2-dimethyl-propylene, trimethylene, etc. Examples of such polyamines include ethylene diamine, diethylene triamine, di(trimethylene)triamine, dipropylene triamine, triethylene tetramine, tripropylene tetramine, tetraethylene pentamine, and pentaethylene hexamine. Such amines encompass isomers such as branched-chain polyamines and the previously mentioned substituted polyamines, including hydrocarbyl-substituted polyamines. Among the polyalkylene polyamines, those containing 2-12 amine nitrogen atoms and 2-24 carbon atoms are especially preferred, and the $C_2$-$C_5$ alkylene polyamines are most preferred, in particular, the lower polyalkylene polyamines, e.g., ethylene diamine, dipropylene triamine, etc.

The polyamine component also may contain heterocyclic polyamines, heterocyclic substituted amines and substituted heterocyclic compounds, wherein the heterocycle comprises one or more 5-6 membered rings containing oxygen and/or nitrogen. Such heterocycles may be saturated or unsaturated and substituted with groups selected from the aforementioned (A), (B), (C) and (D). The heterocycles are exemplified by piperazines, such as 2-methylpiperazine, 1,2-bis-(N-piperazinyl)ethane, and N,N'-bis(N-piperazinyl)piperazine, 2-methylimidazoline, 3-aminopiperidine, 2-aminopyridine, 2-(3-aminoethyl)-3-pyrroline, 3-aminopyrrolidine, N-(3-aminopropyl)morpholine, etc. Among the heterocyclic compounds, the piperazines are preferred.

Typical polyamines that can be used to form the compounds of this invention include the following: ethylene diamine, 1,2-propylene diamine, 1,3-propylene diamine, diethylene triamine, triethylene tetramine, hexamethylene diamine, tetraethylene pentamine, methylaminopropylene diamine, N-(betaaminoethyl)piperazine, N,N'-di(betaaminoethyl)piperazine, N,N'-di(-beta-aminoethyl) imidazolidone-2, N-(beta-cyanoethyl)ethane-1,2-diamine, 1,3,6,9-tetraaminooctadecane, 1,3,6-triamino-9-oxadecane, N-methyl-1,2-propanediamine, 2-(2-aminoethylamino)-ethanol.

Another group of suitable polyamines are the propyleneamines (bisaminopropylethylenediamines). Propyleneamines are prepared by the reaction of acrylonitrile with an ethyleneamine, for example, an ethyleneamine having the formula $H_2N(CH_2CH_2NH)_ZH$ wherein Z is an integer from 1 to 5, followed by hydrogenation of the resultant intermediate. Thus, the product prepared from ethylene diamine and acrylonitrile would be $H_2N(CH_2)_3NH(CH_2)_2NH(CH_2)_3NH_2$.

In many instances the polyamine used as a reactant in the production of succinimides of the present invention is not a single compound but a mixture in which one or several compounds predominate with the average composition indicated. For example, tetraethylene pentamine prepared by the polymerization of aziridine or the reaction of dichloroethylene and ammonia will have both lower and higher amine members, e.g., triethylene tetramine, substituted piperazines and pentaethylene hexamine, but the composition will be largely tetraethylene pentamine and the empirical formula of the total amine composition will closely approximate that of tetraethylene pentamine. Finally, in preparing the succinimide for use in this invention, where the various nitrogen atoms of the polyamine are not geometrically equivalent, several substitutional isomers are possible and are encompassed within the final product. Methods of preparation of polyamines and their reactions are detailed in Sidgewick's "The Organic Chemistry of Nitrogen", Clarendon Press, Oxford, 1966; Noller's "Chemistry of Organic Compounds", Saunders, Philadelphia, 2nd Ed., 1957; and Kirk-Othmer's "Encyclopedia of Chemical Technology", 2nd Ed., especially Volumes 2, pp 99-116.

The reaction of a polyamine with an alkenyl or alkyl succinic anhydride to produce the polyamino alkenyl or alkyl succinimides is well known in the art and is disclosed in U.S. Pat. Nos. 2,992,708; 3,018,291; 3,024,237; 3,100,673; 3,219,666; 3,172,892 and 3,272,746. The above are incorporated herein by reference for their disclosures of preparing alkenyl or alkyl succinimides.

As noted above, the term "polyamino alkenyl or alkyl succinimide" refers to both polyamino alkenyl or alkyl mono- and bis-succinimides and to the higher analogs of polyamino alkenyl or alkyl poly succinimides. Preparation of the bis- and higher analogs may be accomplished by controlling the molar ratio of the reagents. For example, a product comprising predominantly mono- or bis-succinimide can be prepared by controlling the molar ratios of the polyamine and succinic anhydride. Thus, if one mole of polyamine is reacted with one mole of an alkenyl or alkyl substituted succinic anhydride, a predominantly mono-succinimide product will be prepared. If two moles of an alkenyl or alkyl substituted succinic anhydride are reacted per mole of polyamine, a bis-succinimide is prepared. Higher analogs may likewise be prepared.

A particularly preferred class of polyamino alkenyl or alkyl succinimides employed in the instant invention may be represented by Formula II:

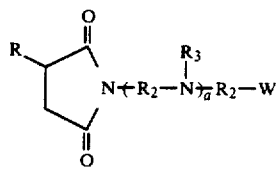

wherein R is alkenyl or alkyl of from 10 to 300 carbon atoms; $R_2$ is alkylene of 2 to 10 carbon atoms; $R_3$ is hydrogen, alkyl of from 1 to 6 carbon atoms or hydroxy alkyl of from 1 to 6 carbon atoms; a is an integer from 0 to 10; and W is $-NH_2$ or represents a group of Formula III:

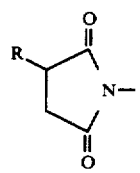

wherein R is alkenyl or alkyl of from 10 to 300 carbon atoms; with the proviso that when W is the group of Formula III above, then a is not zero and at least one of $R_3$ is hydrogen.

As indicated above, the polyamine employed in preparing the succinimide is often a mixture of different compounds having an average composition indicated as the Formula II. Accordingly, in Formula II each value of $R_2$ and $R_3$ may be the same as or different from other $R_2$ and $R_3$.

Preferably R is alkenyl or alkyl of 20 to 300 carbon atoms. In another preferred embodiment, R is preferably 12 to 100 carbon atoms and more preferably 20 to 100 carbon atoms.

Preferably, $R_2$ is alkylene of 2 to 6 carbon atoms and most preferably is either ethylene or propylene.

Preferably, $R_3$ is hydrogen or alkyl of from 1 to 6 carbon atoms.

Preferably, a is an integer from 1 to 6.

In Formula II, the polyamino alkenyl or alkyl succinimides may be conveniently viewed as being composed of three moieties that is the alkenyl or alkyl moiety R, the succinimide moiety represented by the formula:

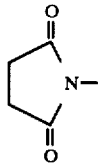

and the polyamino moiety represented by the group

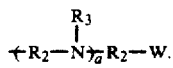

The preferred alkylene polyamines employed in this reaction are generally represented by the formula:

wherein $R_2$ is an alkylene moiety of 2 to 10 carbon atoms and a is an integer from about 0 to 10. However, the preparation of these alkylene polyamines do not produce a single compound and cyclic heterocycles, such as piperazine, may be included to some extent in the alkylene diamines.

B. MODIFIED SUCCINIMIDES

The modified polyamino alkenyl or alkyl succinimides of this invention are prepared by reacting a polyamino alkenyl or alkyl succinimide, IV, with a dihaloformate, V, as shown in reaction (1) below:

wherein $R_8$ and $R_7$ form the remainder of a polyamino alkenyl or alkyl succinimide, Y is either chloro or bromo and $R_4$ and m are as defined above.

As shown in reaction (1) above, the dihaloformate, V, reacts with two primary or secondary amino groups of the same or different polyamino alkenyl or alkyl succinimide. If the dihaloformate reacts with amines of different polyamino alkenyl or alkyl succinimides, the resulting product is "cross-linked". That is, in VI above, the two $R_8R_7N$ groups represent different polyamino alkenyl or alkyl succinimides which are linked together by the

group.

On the other hand, if the dihaloformate reacts with amines of the same polyamino alkenyl or alkyl succinimide, the resulting product is "cyclic". That is, in VI above, the two $R_8R_7N$ groups represents the same polyamino alkenyl or alkyl succinimide.

Below is a simplified reaction scheme illustrating the possible reaction products formed by the process of this invention. It is understood that this reaction scheme is simplified in nature which does not show all possible cross-linked products and is not to be construed in any way as limiting the scope of this invention.

CROSS-LINK PRODUCTS

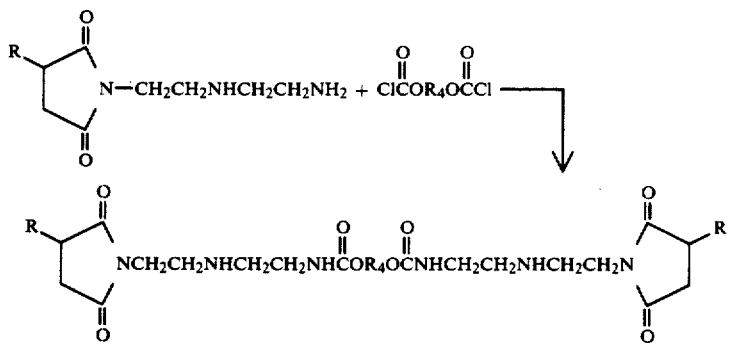

CYCLIC PRODUCTS

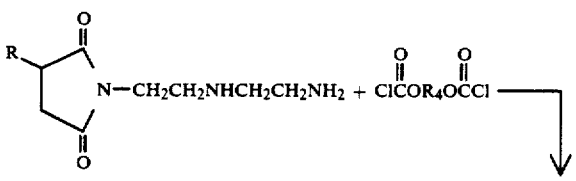

-continued

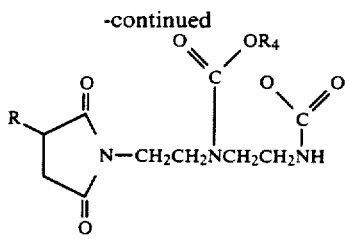

As a result, in reaction (1) above, a mixture of products is formed. This mixture will contain a variety of cross-linked products as well as cyclic products.

Reaction (1) is conducted by contacting the dihaloformate, V, with the polyamino alkenyl or alkyl succinimide, IV. The reaction may be conducted neat or in a suitable inert diluent. Suitable diluents include ethyl acetate, toluene, xylene, oil and the like. An organic base such as pyridine, triethylamine and the like may be added to the reaction to scavenge the acid generated. However, the generated acid may also be removed by an alkaline water wash (pH of from 8–9 or higher) or an alkaline brine wash (pH of from 8–9 or higher) of the reaction solution after reaction completion without the need of added base. The reaction is generally conducted at from 0° C. to 50° C. and is generally complete from within 0.5 to 24 hours. Afterwards, the product may be further isolated by conventional techniques such as chromatography, filtration and the like. If the succinimide contains hydroxyalkyl, use of lower temperature (−78° C. to 0° C.) helps prevent carbonate formation. Carbonates may be removed via reaction with an amine of the succinimide or an alcohol (i.e., ethanol) under transesterification con- ditions.

Alternatively, the modified polyamino alkenyl or alkyl succinimides of this invention can be prepared by reacting a polyamino alkenyl or alkyl succinimide, IV, with a di(alkyl or aryl carbonate) as shown in reaction (1a) below:

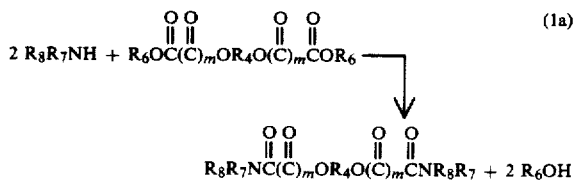

wherein $R_4$, $R_7$, $R_8$ and m are as defined above and $R_6$ is selected from the group consisting of alkyl of 1 to 6 carbon atoms, phenyl and phenyl substituted with 1 to 2 substituents selected from the group consisting of chloro, bromo, nitro, alkyl of from 1 to 6 carbon atoms, and trifluoromethyl. Suitable $R_6$ groups include methyl, ethyl, phenyl, p-nitrophenyl, p-chlorophenyl, 2,4-dichlorophenyl, etc.

Reaction (1a) is conducted by contacting the di(alkyl or aryl carbonate) with the polyamino alkenyl or alkyl succinimide, IV. The reaction may be conducted neat or in a suitable inert diluent. Suitable diluents include toluene, xylene, thinners, oil, and the like. The reaction is generally conducted at from 50° C. to 150° C. and is generally complete from within 1 to 4 hours. Afterwards, the product may be further isolated by conventional techniques such as stripping, chromatography, filtration, and the like.

The di(alkyl or aryl carbonate) is prepared via conventional processes from an alkyl alcohol or an aryl alcohol and the dihaloformate, V, under conditions known per se.

Reaction (1a) likewise produces a mixture of products containing a variety of cross-linked products as well as cyclic products.

In reaction (1) or (1a), the ratio of cross-linked products to cyclic products is of course subject to reaction conditions such as reaction temperature, concentration, etc. For example, by using large amounts of diluent in reaction (1) or (1a), a greater percentage of cyclic products are obtained.

The haloformates of Formula V are prepared as shown in reaction (2) below:

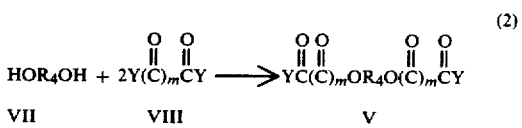

wherein $R_4$, Y and m are as defined above.

This reaction is a conventional process well known in the art and is conducted by employing for m=0 phosgene or carbonyl dibromide and for m=1 oxalyl chloride or oxalyl bromide generally in excess. A mixture of phosgene (or carbonyl dibromide) and oxalyl chloride (or oxalyl bromide) will yield a mixture of products as shown below:

The reaction is conducted by adding the diol, VII, to a suitable diluent such as toluene, benzene, methylene chloride, and the like. The appropriate halogen-containing reagent VIII is then added to the system over a period of time. Alternatively, reagent VIII may be added to the diluent prior to addition of the diol. In general, approximately 2.2–5.0 equivalents of VIII is added per equivalent of diol, VII. The reaction is conducted at from −78° to 50° C., preferably −10° to 10° C., and is generally complete from within ½ to 12 hours. The dihaloformate, V, may be isolated by conventional techniques such as distillation but preferably the system is stripped of a portion of the inert diluent which also removes hydrogen chloride or hydrogen bromide gas generated and excess reagent, VIII. The product, V, contained in the remaining diluent is then used as is reaction (1) above.

As used herein, the term "dihaloformate" includes both the dihaloformate (m=0 of Formula V), the halodicarbonyloxy analogs (m=1 of Formula V), and mixtures thereof.

As used herein, the term "molar charge of dihaloformate to the basic nitrogen of a polyamino alkenyl or alkylsuccinimide" means that the molar charge of dihaloformate employed in the reaction is based upon the theoretical number of basic nitrogens contained in the succinimide. Thus, when 1 equivalent of triethylene tetraamine (TETA) is reacted with an equivalent of succinic anhydride, the resulting mono-succinimide will theoretically contain 3 basic nitrogens. Accordingly, a molar charge of 0.5 would require that 0.5 moles of dihaloformate be added for each basic nitrogen, or in this case, 1.5 moles of dihaloformate for each mole of monosuccinimide prepared from TETA.

Because the dihaloformate and the di(alkyl or aryl carbonate) contain 2 reactive functionalities, the molar charge of the dihaloformate or di(alkyl or aryl carbonate) to the basic nitrogen of the polyamino alkenyl or alkyl succinimide is generally from about 0.1:1 to about 0.5:1 although preferably from about 0.2:1 to about 0.5:1 and most preferably from about 0.35:1 to about 0.5:1.

The diols, VII, are either commercially available or are readily prepared from art recognized techniques. For example, the poly(oxyalkylene) glycol materials, i.e., $HO-R_5-(OR_5)_pOH$, are the addition polymers of lower aliphatic oxides such as ethylene oxide, propylene oxide, the butylene oxides and the pentylene oxides and are prepared by employing a glycol such as ethylene glycol, propylene glycol and the like under polymerization conditions. These materials are commercially available or may be readily prepared.

In the polymerization reaction, a single type of alkylene oxide may be employed, e.g., propylene oxide, in which case the product is a homopolymer, e.g., a poly(oxypropylene) propanol. However, copolymers are equally satisfactory and random copolymers are readily prepared by contacting the hydroxyl-containing compound with a mixture of alkylene oxides, such as a mixture of propylene and butylene oxides. Block copolymers of oxyalkylene units also provide satisfactory poly(oxyalkylene) polymers for the practice of the present invention.

In general, the poly(oxyalkylene) polymers are mixtures of compounds that differ in polymer chain length. However, their properties closely approximate those of the polymer represented by the average composition and molecular weight.

Likewise, hydrocarbyl glycols ($R_4$=hydrocarbyl of from 2 to 30 carbon atoms) are either commercially available or are readily prepared from art recognized techniques.

The modified succinimides of this invention can be reacted at a temperature sufficient to cause reaction with boric acid or a similar boron compound to form borated dispersants having utility within the scope of this invention. In addition to boric acid (boron acid), examples of suitable boron compounds include boron oxides, boron halides and esters of boric acid. Generally from about 0.1 equivalents to 10 equivalents of boron compound to the modified succinimide may be employed.

The modified polyamino alkenyl or alkyl succinimides of this invention are useful as detergent and dispersant additives when employed in lubricating oils. When employed in this manner, the modified polyamino alkenyl or alkyl succinimide additive is usually present in from about 0.2 to 10 percent by weight to the total composition and preferably at about 0.5 to 5 percent by weight. The lubricating oil used with the additive compositions of this invention may be mineral oil or synthetic oils of lubricating viscosity and preferably suitable for use in the crankcase of an internal combustion engine. Crankcase lubricating oils ordinarily have a viscosity of about 1300 CSt 0° F. to 22.7 CSt at 210° F. (99° C.). The lubricating oils may be derived from synthetic or natural sources. Mineral oil for use as the base oil in this invention includes paraffinic, naphthenic and other oils that are ordinarily used in lubricating oil compositions. Synthetic oils include both hydrocarbon synthetic oils and synthetic esters. Useful synthetic hydrocarbon oils include liquid polymers of alpha olefins having the proper viscosity. Especially useful are the hydrogenated liquid oligomers of $C_6$ to $C_{12}$ alpha olefins such as 1-decene trimer. Likewise, alkyl benzenes of proper viscosity such as didodecyl benzene, can be used. Useful synthetic esters include the esters of both monocarboxylic acid and polycarboxylic acids as well as monohydroxy alkanols and polyols. Typical examples are didodecyl adipate, pentaerythritol tetracaproate, di-2-ethylhexyl adipate, dilaurylsebacate and the like. Complex esters prepared from mixtures of mono and dicarboxylic acid and mono and dihydroxy alkanols can also be used.

Blends of hydrocarbon oils with synthetic oils are also useful. For example, blends of 10 to 25 weight percent hydrogenated 1-decene trimer with 75 to 90 weight percent 150 SUS (100° F.) mineral oil gives an excellent lubricating oil base.

Additive concentrates are also included within the scope of this invention. The concentrates of this invention usually include from about 90 to 10 weight percent of an oil of lubricating viscosity and from about 10 to 90 weight percent of the complex additive of this invention. Typically, the concentrates contain sufficient diluent to make them easy to handle during shipping and storage. Suitable diluents for the concentrates include any inert diluent, preferably an oil of lubricating viscosity, so that the concentrate may be readily mixed with lubricating oils to prepare lubricating oil compositions. Suitable lubricating oils which can be used as diluents typically have viscosities in the range from about 35 to about 500 Saybolt Universal Seconds (SUS) at 100° F. (38° C.), although an oil of lubricating viscosity may be used.

Other additives which may be present in the formulation include rust inhibitors, foam inhibitors, corrosion inhibitors, metal deactivators, pour point depressants, antioxidants, and a variety of other wellknown additives.

It is also contemplated the modified succinimides of this invention may be employed as dispersants and detergents in two-cycle oils, hydraulic fluids, marine crankcase lubricants and the like. When so employed, the modified succinimide is added at from about 0.1 to 10 percent by weight to the oil. Preferably, at from 0.5 to 5 weight percent.

When used in fuels, the proper concentration of the additive necessary in order to achieve the desired detergency is dependent upon a variety of factors including the type of fuel used, the presence of other detergents or dispersants or other additives, etc. Generally, however, and in the preferred embodiment, the range of concentration of the additive in the base fuel is 10 to 10,000 weight parts per million, preferably from 30 to 2,000 weight parts per million, and most preferably from 30 to 700 parts per million of the modified succinimide. per part of base fuel. If other detergents are present, a lesser amount of the modified succinimide may be used.

The modified succinimide additives of this invention may be formulated as a fuel concentrate, using an inert stable oleophilic organic solvent boiling in the range of about 150° to 400° F. Preferably, an aliphatic or an aromatic hydrocarbon solvent is used, such as benzene, toluene, xylene or higher-boiling aromatics or aromatic thinners. Aliphatic alcohols of about 3 to 8 carbon atoms, such as isopropanol, isobutylcarbinol, n-butanol and the like, in combination with hydrocarbon solvents are also suitable for use with the fuel additive. In the fuel concentrate, the amount of the additive will be ordinarily at least 10 percent by weight and generally not exceed 70 percent by weight and preferably from 10 to 25 weight percent.

The following examples are offered to specifically illustrate this invention. These examples and illustrations are not to be construed in any way as limiting the scope of this invention.

EXAMPLES

Example 1

Into a 12-liter reaction flask equipped with a mechanical stirrer and a nitrogen sweep was added 4 liters of toluene and 420 g of poly(oxyethylene) glycol [$HO(CH_2CH_2O)_{\sim 4}H$] having an average molecular weight of 200. The system was cooled to 0° C. and 594 g of liquid phosgene was added over a period of about 5 minutes. The system was warmed to room temperature and stirred at room temperature overnight (about 15 hours). At this time, hydrogen chloride gas formed during the reaction as well as excess phosgene were removed by vigorous sparging of the reaction system with nitrogen yielding a toluene solution containing poly(oxyethylene) dichloroformate [i.e.,

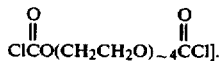
$ClCO(CH_2CH_2O)_{\sim 4}CCl$].

Example 2

Into a 44-liter reaction flask equipped with a mechanical stirrer and a nitrogen sweep was added 8 liters of hexane, 500 g of triethylamine, and 7494 g of a succinimide dispersant composition [prepared by reacting 1 mole of polyisobutenyl succinic anhydride, where the polyisobutenyl group has a number average molecular weight of about 950, with 0.5 moles of tetraethylene pentaamine, then diluting to about 50% actives in diluent oil; having an Alkalinity Value (AV) of approximately 27]. 1158 g of the toluene solution containing the dichloroformate produced in Example 1 was added at room temperature over a period of 1 hour via a dropping funnel. This represents a molar charge of 0.5 moles of dichloroformate per mole of basic nitrogen in the polyamino alkenyl or alkyl succinimide. An additional 4 liters of hexane was then added and the system stirred at room temperature for 1.5 hours. The reaction was then stopped and 8 liters of hexane added to the reaction system. The organic layer was then washed three times with brine-isopropanol solutions. Once with a brine-isopropanol solution prepared by combining 4 liters of water, 3 liters of isopropanol, 6 liters of brine and 2 lbs of salt and then twice with brine-isopropanol solutions prepared by combining 4 liters of water, 2 liters of isopropanol, 4 liters of brine and 1 lb of salt. The organic solution was then dried over anhydrous magnesium sulfate, filtered and stripped to yield a modified succinimide of this invention having an Alkalinity Value (AV) of 9.9.

Example 3

Into a 44-liter reaction flask equipped with a mechanical stirrer and a nitrogen sweep was added 1000 gm of triethylamine, 20 liters of hexane and 6691 g of a succinimide dispersant composition [prepared by reacting 1 mole of polyisobutenyl succinic anhydride, where the polyisobutenyl group has a number average molecular weight of about 950, with 0.87 moles of tetraethylene pentaamine, then diluting to about 38% actives in diluent oil; having an Alkalinity Value (AV) of approximately 44]. 1377 g of a dichloroformate

$ClCO(CH_2CH_2O)_{\sim 4}CCl$]

in 819 g of toluene (prepared in a manner similar to that of Example 1) was added at room temperature over a period of 1 hour via a dropping funnel. This represents a molar charge of 0.5 moles of dihaloformate per mole of basic nitrogen in the polyamine alkenyl or alkyl succinimide. The system stirred at room temperature for 1.5 hours. The reaction was then stopped and 8 liters of hexane added to the reaction system. The organic layer was then washed three times with brine-isopropanol solutions. Once with a brine-isopropanol solution prepared by combining 4 liters of water, 3 liters of isopropanol, 6 liters of brine and 2 lbs of salt and then twice with brine-isopropanol solutions prepared by combining 4 liters of water, 2 liters of isopropanol, 4 liters of brine and 1 lb of salt. The organic solution was then dried over anhydrous magnesium sulfate, filtered and stripped to yield a modified succinimide of this invention having an Alkalinity Value (AV) of 13.1.

Example 4

Into a 1-liter three-neck flask equipped with a mechanical stirrer and nitrogen sweep is placed 200 ml of toluene. The system is cooled to 0° C. and phosgene gas is bubbled in until 21.9 g (0.22 moles) is contained in the toluene. At this time, 60 g (0.1 mole) of poly(oxyethylene) glycol [$HO(CH_2CH_2O)_{\sim 13}H$] having an average molecular weight of 600 is added over 30 minutes. The system is warmed to room temperature and stirred at room temperature for two hours. At this time, excess phosgene is removed by vigorous sparging of the reaction system with nitrogen for two hours yielding a toluene solution containing poly(oxyethylene) dichloroformate, [i.e.,

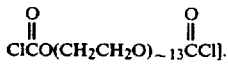
$ClCO(CH_2CH_2O)_{\sim 13}CCl$].

The toluene solution containing the dichloroformate derivative is then added to a composition containing 200 ml methylene chloride, 30 ml triethylamine and 406 g of a succinimide dispersant composition [prepared by reacting 1 mole of polyisobutenyl succinic anhydride, where the polyisobutenyl group has a number average molecular weight of about 950, with 0.87 mole of tetraethylene pentaamine; then diluting to about 40% actives with diluent oil]. The system is stirred at room temperature for two hours. Afterwards, the system is partially stripped, diluted with 1-liter hexane, extracted twice with brine (pH 8-9), dried (MgSO4), filtered and stripped to afford a modified polyamino alkenyl or alkyl succinimide of this invention.

Example 5

Into a 1-liter three-neck flask equipped with a mechanical stirrer and nitrogen sweep is placed 200 ml of methylene chloride containing 18.9 g of oxalyl chloride (0.128 mole). To this mixture at room temperature is added dropwise a solution of methylene chloride containing 21.25 g (0.05 mole) of poly(oxypropylene) glycol, having an average molecular weight of 425, over a period of 30 minutes. Upon completion of addition, the solution is stripped to remove methylene chloride and excess oxalyl chloride yielding the di(chlorodicarbonyloxy) derivative

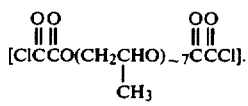

The methylene chloride solution containing the di(-chlorodicarbonyloxy) derivative is then added to a composition containing 200 ml methylene chloride, 30 ml triethylamine and 406 g of a succinimide dispersant composition [prepared by reacting 1 mole of polyisobutenyl succinic anhydride, where the polyisobutenyl group has a number average molecular weight of about 950, with 0.87 mole of tetraethylene pentaamine; then diluting to about 35% actives with diluent oil]. The system is stirred at room temperature for two hours afterwards, the system is partially stripped, diluted with 1-liter hexane, extracted twice with brine (pH 8-9), dried (MgSO4), filtered and stripped to afford a modified polyamino alkenyl or alkyl succinimide of this invention.

Example 6

Into a 22-liter reaction flask equipped with a mechanical stirrer and a nitrogen sweep was added 8 liters of hexane, 200 g of triethylamine, and 4393 g of a succinimide dispersant composition [prepared by reacting 1 mole of polyisobutenyl succinic anhydride, where the polyisobutenyl group has a number average molecular weight of about 950, with 0.5 moles of tetraethylene pentaamine, then diluting to about 50% actives in diluent oil; having an alkalinity value (AV) of approximately 27]. 250 Grams of the dichloroformate produced similarly to Example 1 (in 65 ml of toluene) was added at room temperature over a period of 20 minutes via a dropping funnel. This represents a molar charge of 0.25 moles of dichloroformate per mole of basic nitrogen. The system was stirred at room temperature for 1.5 hours. At this time, 4 liters of hexane as well as 2 liters of water were added to the system. The reaction system was stirred for 5 minutes. Afterwards, 1.5 liters of isopropanol, 1 liter of brine and 1 lb. of salt were added to the system and the system stirred for 15 minutes. After settling, the aqueous layer was removed, the cuff (the layer between the aqueous layer and the organic layer) was separated and saved and the organic layer saved. To the cuff was added 2 liters of hexane and then the solution stirred. After settling, the aqueous layer and any remaining cuff were removed and the organic solutions combined. The combined organic solutions were washed twice with slightly alkaline brine, i.e., pHf9-10. The organic solution was then dried over anhydrous magnesium sulfate, filtered and stripped to yield a modified succinimide of this invention having an alkalinity value (AV) of 12.9.

Example 7

A. Into a 2-liter three-neck flask equipped with a mechanical stirrer and nitrogen sweep is placed 400 ml of toluene. The system is cooled to 0° C. and phosgene gas is bubbled in until 43.8 g (0.44 moles) is contained in the toluene. At this time, 34.8 g (0.2 moles) of 1,10-decanediol is added over 30 minutes. The system is warmed to room temperature and stirred at room temperature for two hours. At this time, excess phosgene is removed by vigorous sparging of the reaction system with nitrogen for two hours yielding a toluene solution containing the dichloroformate derivative

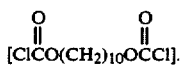

B. Into a 2-liter three-neck round bottom flask is added 37.6 g (0.4moles) phenol, 31.6 g of pyridine and 150 ml of toluene. The system is stirred at room temperature and over a period of 40 minutes the toluene solution containing the dichloroformate derivative of A above is added. After reaction completion, the product is extracted with hexane. The organic layer is washed three times with brine and dried over anhydrous magnesium sulfate. The solvent is removed to yield the dicarbonate:

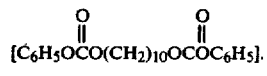

C. 82.8 g of the dicarbonate

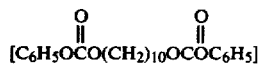

is added to a 2-liter reaction flask together with 377 g of a succinimide dispersant composition [prepared by reacting 1 mole of polyisobutenyl succinic anhydride, where the polyisobutenyl group has a number average molecular weight of about 950, with 0.5 mole of tetraethylene pentaamine; then diluting to about 50% actives in diluent oil]. The system is then heated to 165° C. and stirred under a nitrogen atmosphere for 2.66 hours to afford a modified polyamino alkenyl or alkyl succinimide of this invention.

In a manner similar to Example 6 above, the following compounds may be used in place of phenol in preparing the dicarbonate suitable for reaction with a polyamino alkenyl or alkyl succinimide:

methanol; ethanol; n-propanol; isopropanol; 4-methylphenol; 4-ethylphenol, 4-chlorophenol; 2-chlorophenol; 4-bromophenol; 2-bromophenol; 2,4-dichlorophenol; 2,4-dibromophenol; 2,4,6-trichlorophenol; 2,4,6-tribromophenol 3-(trifluoromethyl)-phenol; etc.

Example 8

Formulated oils containing different modified succinimides of the invention were tested in a Sequence V-D Test method (according to candidate test for ASTM). This procedure utilizes a Ford 2.3-liter, fourcylinder Pinto engine. The test method simulates a type of severe field test service characterized by a combination of low speed, low temperature "stop and go" city driving and moderate turnpike operation. The effectiveness of the additives in the oil is measured in terms of the protection against sludge and varnish deposits on a 0 to 10 scale with 0 being black and 10 indicating no varnish or sludge deposits. The result are indicated in Table I.

The comparisons were made in a formulated oil containing a succinimide dispersant, 20 mmoles of an overbased calcium phenate, 30 mmoles as an overbased calcium sulfonate, 0.16% zinc as primary alkyl zinc dithiophosphate, and a nondispersant ethylene-propylene copolymer VI improver to give an SAE 10W40 oil.

TABLE I

| Formulation Containing 6% Succinimide of Example | Average Varnish | Average Sludge |
|---|---|---|
| Starting Succinimide of Examples 2 and 6 | 4.7[1] | 9.5 (typical) |
| Example 2 | 6.4[1] | 9.5[1] |
| Example 6 | 6.9[2] | 9.2[2] |

[1] Average of two runs
[2] One run only

Example 9

Compositions of this invention were tested in a Caterpillar 1-G2 test in which a single-cylinder diesel engine having a 5⅛" bore by 6½" stroke is operated under the following conditions: timing, degrees BTDC, 8; brake mean effective pressure, psi 1451; brake horsepower 42; Btu's per minute 5850; speed 1800 RPM; air boost, 53" Hg absolute, air temperature in, 255° F.; water temperature out, 190° F.; and sulfur in fuel, 0.4%. At the end of each 12 hours of operation, sufficient oil is drained from the crankcase to allow addition of 1 quart of new oil. In the test on the lubricating oil compositions of this invention, the 1-G2 test is run for 60 hours. At the end of the noted time period, the engine is dismantled and rated for cleanliness. These results are reported below. Lower values represent cleaner engines.

The base oil used in these tests is a mid-Continent base stock SAE 30 oil containing 18 mmols/kg of a zinc dihydrocarbyl dithiophosphate, 36 mmls/kg of an overbased calcium phenate, and the amount noted in the table of dispersant.

| Test Results - 1-G2 Caterpillar Test (60 Hours) | | |
|---|---|---|
| 6% Dispersant of Example | Top Groove fill, % | Weighted Total Demerits (WTD) |
| Starting Succinimide of Examples 2 and 6 | 55[1] | 255[1] |
| Example 2 | 71[1] | 274[1] |
| Example 6 | 60[2] | 591[2] |

[1] Average of 2 runs
[2] One run only

What is claimed is:

1. A fuel composition comprising a hydrocarbon boiling in the gasoline or diesel range and from about 10 to 10,000 parts per million of a product produced by the process which comprises contacting at a temperature sufficient to cause reaction a polyamino alkenyl or alkyl succinimide having at least one primary or secondary amino group with a compound of the Formula V:

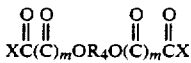

wherein $R_4$ is selected from the group consisting of a divalent hydrocarbyl of from 2 to 30 carbon atoms with the proviso that the hydrocarbyl carbon atom bound to one

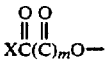

group is not also bound to the other

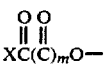

group and $-R_5+OR_5+_p$ wherein $R_5$ is alkylene of from 2 to 5 carbon atoms and p is an integer of from 1 to 100; X is selected from the group consisting of bromo, chloro and $-OR_6$ wherein $R_6$ is selected from the group consisting of alkyl of from 1 to 6 carbon atoms, phenyl and phenyl substituted with 1 to 2 substituents selected from the group consisting of chloro, bromo, nitro, alkyl of from 1 to 6 carbon atoms and trifluoromethyl; and m is independently an integer of from 0 to 1 and wherein the molar charge of the compound of Formula V to the basic nitrogen of the polyamino alkenyl or alkyl succinimide is from about 0.1:1 to about 0.5:1.

2. A fuel composition according to claim 1 wherein the alkenyl or alkyl moiety of the polyamino alkenyl or alkyl sucinimide is from about 20 to 300 carbon atoms.

3. A fuel composition according to claim 2 wherein $R_4$ is a straight-chain alkylene group of from 2 to about 30 carbon atoms or a branched-chain alkylene group of from 3 to about 30 carbon atoms.

4. A fuel composition according to claim 3 wherein $R_4$ is a straight-chain alkylene group of from 2 to about 30 carbon atoms.

5. A fuel composition according to claim 4 wherein m is 0.

6. A fuel composition according to claim 5 wherein m is 1.

7. A fuel composition according to claim 2 wherein $R_4$ is $-R_5+OR_5+_p$ wherein $R_5$ is alkylene of from 2 to 5 carbon atoms and p is an integer from 1 to 100.

8. A fuel composition according to claim 7 wherein $R_5$ is alkylene of from 2 to 4 carbon atoms.

9. A fuel composition according to claim 8 wherein p is an integer from 1 to 50.

10. A fuel composition according to claim 9 wherein p is an integer from 2 to 20.

11. A fuel composition according to claim 10 wherein m is 0.

12. A fuel composition according to claim 10 wherein m is 1.

13. A fuel composition comprising a hydrocarbon boiling in the gasoline or diesel range and from about 10 to 10,000 parts per million of a product produced by the process which comprises contacting at a temperature sufficient to cause reaction a polyamino alkenyl or alkyl succinimide of the Formula II:

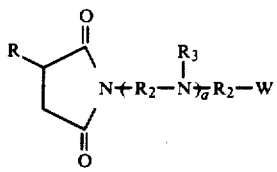

wherein R is alkenyl or alkyl of from 10 to 300 carbon atoms; $R_2$ is alkylene of 2 to 10 carbon atoms; $R_3$ is hydrogen, alkyl of 1 to 6 carbon atoms or hydroxy alkyl of 1 to 6 carbon atoms; a is an integer from 0 to 10; and W is —$NH_2$ or represents a group of Formula III:

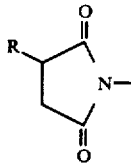

wherein R is alkenyl or alkyl of from 10 to 300 carbon atoms with the proviso that when W is the group of Formula III above, then a is not zero and at least one of $R_3$ is hydrogen; with a compound of Formula V:

wherein $R_4$ is selected from the group consisting of a divalent hydrocarbyl group of from 2 to 30 carbon atoms with the proviso that the hydroarbyl carbon atom bound to one

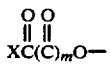

group is not also bound to the other

group and —$R_5$-(-$OR_5$-)$_p$ wherein $R_5$ is alkylene of from 2 to 5 carbon atoms and p is an integer of from 1 to 100; X is selected from the group consisting of bromo, chloro and —$OR_6$ wherein $R_6$ is selected from the group consisting of alkyl of from 1 to 6 carbon atoms, phenyl and phenyl substituted with 1 to 2 substituents selected from the group consisting of chloro, bromo, nitro, alkyl of from 1 to 6 carbon atoms and trifluromethyl; and m is independently an integer of from 0 to 1 and wherein the molar charge of the compound of Formula V to the basic nitrogen of the polyamino alkenyl or alkyl succinimide is from about 0.1:1 to about 0.5:1.

14. A fuel composition according to claim 13 wherein R is alkenyl or alkyl of from 20 to 100 arbon atoms.

15. A fuel composition according to claim 14 wherein $R_2$ is alkylene of from 2 to 6 carbon atoms and a is an integer of from 1 to 6.

16. A fuel composition according to claim 15 wherein W is

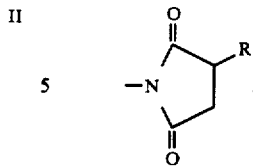

17. A fuel composition according to claim 16 wherein $R_4$ is a straight-chain alkylene group of from 2 to about 30 carbon atoms or a branched-chain alkylene group of from 3 to about 30 carbon atoms.

18. A fuel composition according to claim 17 wherein m is 0.

19. A fuel composition according to claim 18 wherein X is chloro.

20. A fuel compositon according to claim 17 wherein m is 1.

21. A fuel composition according to claim 20 wherein X is chloro.

22. A fuel composition according to claim 16 wherein $R_4$ is —$R_5$-(-$OR_5$-)$_p$ wherein $R_5$ is alkylene of from 2 to 5 carbon atoms and p is an integer from 1 to 100.

23. A fuel composition according to claim 22 wherein $R_5$ is alkylene of from 2 to 4 carbon atoms and p is an integer of from 2 to 20.

24. A fuel composition according to claim 23 wherein m is 0.

25. A fuel composition according to claim 24 wherein X is chloro.

26. A fuel composition according to claim 23 wherein m is 1.

27. A fuel composition according to claim 26 wherein X is chloro.

28. A fuel concentrate comprising a stable inert oleophilic organic solvent boiling in the range of about 150° F. to 400° F. and from about 10 to 70 weight percent of a product produced by the process which comprises contacting at a temperature sufficient to cause reaction a polyamino alkenyl or alkyl succinimide having at least one primary or secondary amino group with a compound of the Formula V:

wherein $R_4$ is selected from the group consisting of a divalent hydrocarbyl of from 2 to 30 carbon atoms with the proviso that the hydrocarbyl carbon atom bound to one

group is not also bound to the other

group and $R_5$-(-$OR_5$-)$_p$ wherein $R_5$ is alkylene of from 2 to 5 carbon atoms and p is an integer of from 1 to 100; X is selected from the group consisting of bromo, chloro and —$OR_6$ wherein $R_6$ is selected from the group consisting of alkyl of from 1 to 6 carbon atoms, phenyl and phenyl substituted with 1 to 2 substituents selected from the group consisting of chloro, bromo, nitro, alkyl of from 1 to 6 carbon atoms and trifluoromethyl; and m is independently an integer of from 0 to 1 and wherein the molar charge of the compound of Formula V to the basic nitrogen of the polyamino alkenyl or alkyl succinimide is from about 0.1:1 to about 0.5:1.

29. A fuel concentrate according to claim 28 wherein the alkenyl or alkyl moiety of the polyamino alkenyl or alkyl succinimide is from about 20 to 300 carbon atoms.

30. A fuel concentrate according to claim 29 wherein $R_4$ is $R_5$–$(OR_5)_p$ wherein $R_5$ is alkylene of from 2 to 5 carbon atoms and p is an integer from 1 to 100.

31. A fuel concentrate according to claim 30 wherein p is an integer from 2 to 20.

32. A fuel concentrate according to claim 31 wherein m is zero.

33. A fuel concentrate comprising a stable inert olephilic organic solvent boiling in the range of about 150° F. to 400° F. and from about 10 to 70 weight percent of a product produced by the process which comprises contacting at a temperature sufficient to cause reaction a polyamino alkenyl or alkyl succinimide of the Formula II:

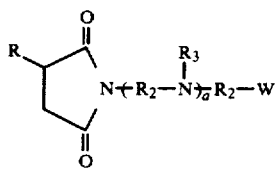   II wherein R is alkenyl or alkyl of from 10 to 300 carbon atoms; $R_2$ is alkylene of 2 to 10 carbon atoms; $R_3$ is hydrogen, alkyl of 1 to 6 carbon atoms or hydroxyalkyl of 1 to 6 carbon atoms; a is an integer from 0 to 10; and W is —$NH_2$ or represents a group of Formula III:

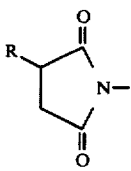   III wherein R is alkenyl or alkyl of from 10 to 300 carbon atoms with the proviso that when W is the group of Formula III above, then a is not zero and at least one of $R_3$ is hydrogen; with a compound of Formula V:

   V wherein $R_4$ is selected from the group consisting of a divalenet hydrocarbyl group of from 2 to 30 carbon atoms with the proviso that the hydrocarbyl carbon atom bound to one

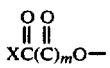

group is not also bound to the other

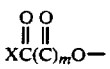

group and $R_5$–$(OR_5)_p$ wherein $R_5$ is alkylene of from 2 to 5 carbon atoms and p is an integer of from 1 to 100; X is selected from the group consisting of bromo, chloro, and —$OR_6$ wherein $R_6$ is selected from the group consisting of alkyl of from 1 to 6 carbon atoms, phenyl and phenyl substituted with 1 to 2 substituents selected from the group consisting of chloro, bromo, nitro, alkyl of from 1 to 6 carbon atoms and trifluoromethyl; and m is independently an integer of from 0 to 1 and wherein the molar charge of the compound of Formula V to the basic nitrogen of the polyamino alkenyl or alkyl succinimide is from about 0.1:1 to about 0.5:1.

34. A fuel concentrate according to claim 33 wherein R is alkenyl or alkyl of from 20 to 100 carbon atoms.

35. A fuel concentrate according to claim 34 wherein $R_2$ is alkylene of 2 to 6 carbon atoms and a is an integer of from 1 to 6.

36. A fuel concentrate according to claim 35 wherein W is

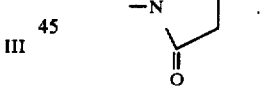

37. A fuel concentrate according to claim 36 wherein $R_4$ is $R_5$–$(OR_5)_p$ wherein $R_5$ is alkylene of from 2 to 5 carbon atoms and p is an integer from 1 to 100.

38. A fuel concentrate according to claim 37 wherein $R_5$ is alkylene of from 2 to 4 carbon atoms and p is an integer of from 2 to 20.

39. A fuel concentrate according to claim 38 wherein m is zero.

* * * * *

UNITED STATES PATENT AND TRADEMARK OFFICE
CERTIFICATE OF CORRECTION

Page 1 of 2

PATENT NO. : 4,710,201
DATED : December 1, 1987
INVENTOR(S) : Thomas F. Buckley

It is certified that error appears in the above-identified patent and that said Letters Patent are hereby corrected as shown below:

Columns 11/12, lines 1-10 " 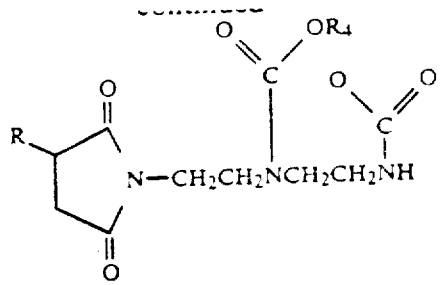

should read -- 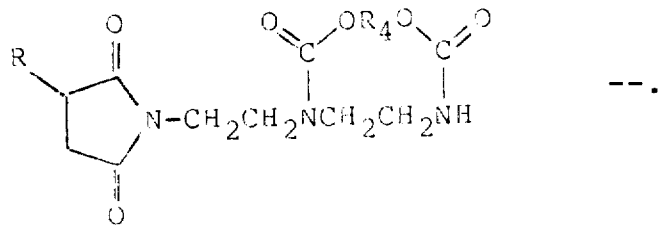 --.

UNITED STATES PATENT AND TRADEMARK OFFICE
CERTIFICATE OF CORRECTION

PATENT NO. : 4,710,201

DATED : December 1, 1987

INVENTOR(S) : Thomas F. Buckley

It is certified that error appears in the above-identified patent and that said Letters Patent is hereby corrected as shown below:

Column 21, line 35, "hydroarbyl" should read -- hydrocarbyl --.

Column 21, line 63, "arbonatoms" should read -- carbon atoms --.

Signed and Sealed this

Seventh Day of June, 1988

*Attest:*

DONALD J. QUIGG

*Attesting Officer*　　　　*Commissioner of Patents and Trademarks*